(12) United States Patent
Margetis et al.

(10) Patent No.: US 9,615,618 B2
(45) Date of Patent: Apr. 11, 2017

(54) SYSTEM AND METHOD FOR HEAD AND SPINE IMMOBILIZATION AND PROTECTION

(71) Applicants: Konstantinos Margetis, New York, NY (US); Thomas Mroz, Cleveland, OH (US)

(72) Inventors: Konstantinos Margetis, New York, NY (US); Thomas Mroz, Cleveland, OH (US)

( * ) Notice: Subject to any disclaimer, the term of this patent is extended or adjusted under 35 U.S.C. 154(b) by 31 days.

(21) Appl. No.: 14/573,640

(22) Filed: Dec. 17, 2014

(65) Prior Publication Data

US 2015/0164171 A1  Jun. 18, 2015

Related U.S. Application Data

(60) Provisional application No. 61/917,558, filed on Dec. 18, 2013.

(51) Int. Cl.
*A42B 3/04* (2006.01)
*A61F 5/37* (2006.01)

(52) U.S. Cl.
CPC .......... *A42B 3/0473* (2013.01); *A61F 5/3707* (2013.01)

(58) Field of Classification Search
CPC ........ A61F 5/37; A61F 5/3707; A42B 3/0473; A41D 13/0512; A63B 2220/40; A63B 71/10

See application file for complete search history.

(56) References Cited

U.S. PATENT DOCUMENTS

| | | | |
|---|---|---|---|
| 1,276,117 A * | 8/1918 | Riebe | F16C 1/26 138/120 |
| 3,546,961 A * | 12/1970 | Marton | B63C 11/26 74/502.5 |
| 5,287,562 A * | 2/1994 | Rush, III | A41D 13/018 2/413 |
| 5,371,905 A | 12/1994 | Keim | |
| 5,546,609 A * | 8/1996 | Rush, III | A41D 13/018 2/413 |
| 6,729,643 B1 | 5/2004 | Bassick et al. | |
| 6,968,576 B2 | 11/2005 | McNeil et al. | |
| 7,634,874 B2 * | 12/2009 | Lucas | E04H 4/082 52/108 |
| 7,703,152 B2 * | 4/2010 | Rhodes | A42B 3/0473 2/421 |
| 8,057,415 B2 | 11/2011 | Hipp et al. | |

(Continued)

*Primary Examiner* — Anna Kinsaul
*Assistant Examiner* — Jocelyn Wu
(74) *Attorney, Agent, or Firm* — Kramer Levin Naftalis & Frankel LLP

(57) ABSTRACT

The present invention relates to a device that stabilizes and/or protects the head and spine from injuries. An immobilization device includes one or more pillars with multiple segments that protect the head and spine of a user. The pillars typically run along the part of the head and spine and pelvis that the device protects. A wire or cable runs through these segments in the pillars. By design, when the pillars of the invented system are not activated and the system is in normal use, the pillars are designed to be as flexible as possible and allow full physiologic motion of the protected body part. Activation of the system confers rigidity to the system and prevents or lessens harmful, non-physiologic motion of the body part intended to be protected.

16 Claims, 14 Drawing Sheets

(56) References Cited

U.S. PATENT DOCUMENTS

| | | |
|---|---|---|
| 8,181,281 B2 | 5/2012 | Nagely et al. |
| 8,834,394 B2 | 9/2014 | Ghajar |
| 2008/0209617 A1* | 9/2008 | Castillo ................ A42B 3/0473 2/461 |
| 2011/0277225 A1* | 11/2011 | Salkind .............. A41D 13/0512 2/461 |
| 2012/0279311 A1 | 11/2012 | Helmer et al. |
| 2014/0224849 A1* | 8/2014 | Hiemenz ................... A45F 3/04 224/271 |
| 2014/0323921 A1* | 10/2014 | Huang ................ A61B 5/4064 600/587 |
| 2015/0157080 A1* | 6/2015 | Camarillo ............ A42B 3/0473 2/459 |

* cited by examiner

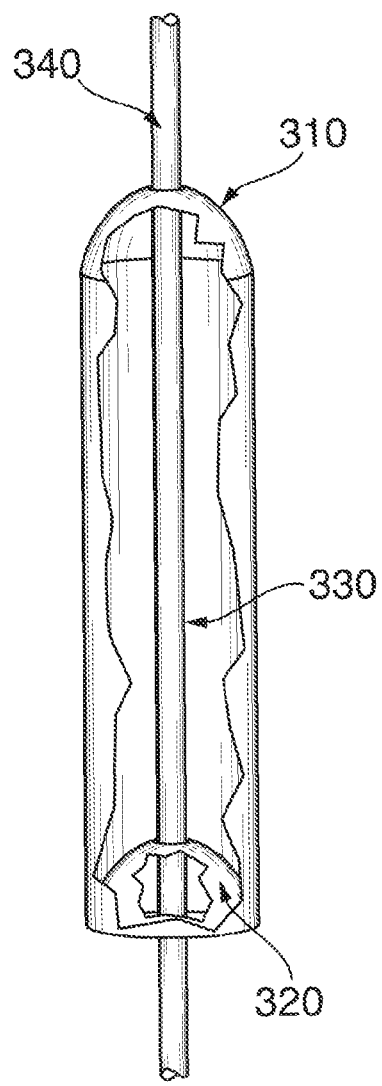
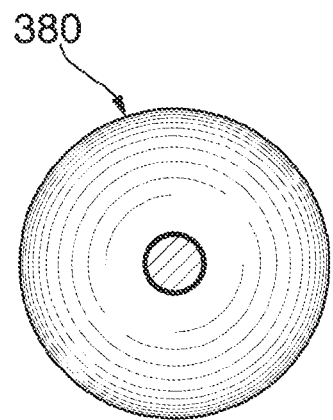
FIG. 3A
FIG. 3B

SYSTEM AND METHOD FOR HEAD AND SPINE IMMOBILIZATION AND PROTECTION

PRIORITY REFERENCE TO PROVISIONAL APPLICATION

This application claims benefit and hereby incorporates by reference provisional application Ser. No. 61/917,558, entitled "System and Method for Head and Spine Immobilization and Protection," filed on Dec. 18, 2013 by inventor Konstantinos Margetis.

BACKGROUND

Spine and traumatic brain injuries cause significant morbidity and mortality due to events both in the civilian and military field. From a civilian perspective, extreme sporting enthusiasts are at risk for head and spinal injuries due to direct impacting or to non-physiologic, harmful extremes of motion. From a military perspective, spine injuries and traumatic brain injuries can occur as a result of explosions. Such blast injuries can be divided into four main categories:
  Primary: Caused by the direct effect of blast overpressure on tissue of a victim. In some situations the blast will cause a differential acceleration of the head in relation to the body, because the body might be heavier (e.g. due to equipment carried) or because it might be protected (e.g. in armored vehicles' hatches or in trenches).
  Secondary: Caused by fragments or flying objects (e.g. rubble, building fragments, and shrapnel) that strike people.
  Tertiary: Occurs when blast victims fly through the air and strike other objects or the ground.
  Quaternary: Includes smoke and debris inhalation, burns and any injury not previously described.

Currently, there is no head and spine protection device with widespread acceptance for protecting from spine and traumatic brain injuries when a user is subject to sudden accelerations or decelerations in the military or civilian arena. Some protective devices have increased the survivability from traumatic events due to spine and traumatic brain injuries in accidents that would have been fatal otherwise. Some protective devices protect the spine but these devices are bulky, heavy and significantly reduce the range of motion of the cervical spine (e.g. systems based on rods). Other protective devices provide limited stabilization (e.g. air bags—also prone to puncture or might cause injury from sudden inflation) or significantly reduce the range of motion (e.g. collars worn by race car drivers that only allow limited head turning). Accordingly, there remains a need for a lightweight, mobile, and effective device that protects a user from spine and traumatic brain injuries in accidents without significantly restricting the motion of the user while in everyday use.

SUMMARY OF THE INVENTION

There are three primary fields of application for the described invention. First, to protect the spine, head and brain of a user from harmful forces that cause non-physiologic motion, including, acceleration or deceleration. Second, to protect the head and brain of a user from impacting objects, such as rocks, shrapnel or other debris. Third, to immobilize the head and neck of a user for comfort.

An immobilization device includes one or more pillars with multiple metallic (e.g. steel, titanium, or aluminum or metal alloys), or synthetic (e.g. carbon fiber, ceramics, polymer, viscoelastic, rubber, plastic) segments that protect the head and spine of a user. The pillars typically run along the part of the head and spine and pelvis that the device protects. A wire or cable runs through these segments in the pillars. By design, when the pillars of the invented system are not activated and the system is in normal use, the pillars are designed to be as flexible as possible and allow full physiologic motion of the protected body part. Activation of the system confers rigidity to the system and prevents or lessens harmful, non-physiologic motion of the body part intended to be protected.

Activation of the immobilization devices is accomplished by a mechanism to rapidly cause the flexible, inactivated pillars to become rigid. The segments within the pillars can have a variety of shapes. Such shapes include, but are not limited to, cylindrical, cuboid, triangular or cone, and combinations and variations of these shapes. The shape of the segments may be symmetric or asymmetric and be designed in such a way to allow preferential motion (e.g. more flexion and less extension). A hollow lumen runs the length of the segments in the elongated dimension through which a wire or cable can be placed. The segments are strung together one after another, similar to links of a necklace. In some embodiments, an articulation between adjacent segments will help maintain orientation of the individual segments relative to one another, during system activation and deactivation. In most applications, it is preferable for the segments to be durable, heat resistant, compact and lightweight. In some example embodiments, one end of the segments are convex and the other end concave. The convex and concave ends may be spherical, triangular, rectangular or other geometrical shape of various dimensions. Further, they may be asymmetric to confer more rigidity in the activated state. As such, when the segments are used in a pillar, each end of a segment articulates with the respective end of the adjacent segment (i.e. in the case of spherical terminal ends, the concave ends articulate with convex ones). In the example embodiments where an inelastic wire or cable runs through the lumen of the segments, the wire or cable and segments can be tightened causing the segments to contract together, locking the segments together and causing the pillar(s) to become rigid. The surface of the concave and convex surfaces may be smooth or textured, and may be coated with a special material or enamel designed to provide the optimal friction between the two articulating ends.

In some embodiments, system activation causes a sudden translation of the segments and/or cable(s). Such translation causes impaction of one segment onto its adjacent segment(s). The interlocking geometry, articulating surfaces of the segments, materials of the segments, tightening forces and other variables work in concert, then, to confer the desired rigidity to the system. This translation, and subsequent locking of the wire(s) or cable(s) and segments into the activated, rigid state, occur in the housing mechanism located in chest regions (e.g. vest), in the pelvic apparatus, or as part of an exoskeleton.

In some example embodiments when activation, or rigidity, of the system needs to be rapid a number of mechanisms can be employed to activate the system. These include, but are not limited to, a pyrotechnic, compressed gas, electric, magnetic, electromagnetic, hydraulic, and/or mechanical (e.g. spring or band mechanisms) devices. The example mechanisms can provide the necessary tightening force, thus conferring the desired stability to the head relative to the body and/or to various regions of the spine. In other example embodiments and applications where rapid activation is not necessary, activation and deactivation of the system is caused by manually tightening or loosening of the wire or cable and segments. Examples of how this can be done include, but are not limited to, an electric motor or a hand crank or a release cord.

Activation of this immobilization device can be triggered by various types of signaling between sensors, microprocessors, receivers, and other mechanisms built into a helmet (or other type of device on the head), a vest, pelvic harness, clothing, and/or vehicle. Examples of signaling include, but are not limited to, wires, fuses, radiofrequency, electric, or magnetic. Examples of the sensors include, but are not limited to light sensors, sound sensors, accelerometers or other motion sensor, pressure sensors (i.e. manometers), heat sensors and gyroscopes.

In some example embodiments, activation of one, or multiple, immobilization devices can be done remotely, or automatically, in a predetermined and secure manner. An example is a group of soldiers using the immobilization device that are, as a group, exposed to a blast. As one soldier's device closest to the blast is activated first, other devices worn by soldiers in what is deemed to be a dangerous perimeter to him/her can be activated, too, prior to the actual physical effects of the blast are experienced. In this case, the immobilization devices include wireless communication circuitry allowing communication between the immobilization devices.

In some example embodiments, the pillars connect to or span a portion or portions of the body intended to be protected. Connection to the head of the user will involve the pillars attaching in some way to a helmet, brace, band, or other device worn on the user's head. Such attachments can be anterior, lateral, or on the posterior aspect of the said device. There may be a single attachment point, or multiple attachment points. On the lower end of the user, the pillars attach either to a housing apparatus built into a vest in the upper or lower trunk (anterior or posterior) region of the user and/or to a belt or specialized harness in the pelvic region. As mentioned the housing for the pillars may be built into a vest or may be a free standing apparatus, or harness, apart from a vest, worn by the user.

In some example embodiments, the system includes telescoping, pistoning, swiveling and/or rotating mechanism of the pillars to facilitate full, unimpeded motion of the head, neck, or mid and lower back when the device is not activated. This mechanism can be built into the helmet, vest or pelvic apparatus.

When the system is activated, the protected body parts are stabilized through the increase rigidity of the pillars. In the case of the head and neck protection, upon activation, the head and neck are stabilized and movement of the head and neck is prevented or minimized when the system is activated (i.e. when the pillar(s) are rigid). The pillars can confer different levels of rigidity depending of the circumstances and the intended application of the immobilization device. The pillars can be deactivated manually or automatically (e.g. after a predetermined time lapse or after harmful forces no longer detected). The rate of deactivation can be instantaneous or gradual.

The system may allow for multiple, sequential activation and deactivation cycles. The deactivation, again, can be manual or automatic. For example, automatic deactivation can be caused by a predetermined time lapse or when the dangerous forces or conditions causing the activation are no longer detected. In this way, for example, an extreme sporting individual or combat soldier or downhill skier using the device will be able to return to their activity during extreme or hazardous conditions.

In some embodiments, the pillars may have a protective sheath, sleeve, or covering, to prevent buildup of dirt, sediment, or other material or substance that could interfere with the desired function. The sheaths or sleeves composition can include materials including, but not limited to, plastic, cloth, metal, or silicone.

In some example embodiments, the immobilization system described herein allows the spine of the user to retain its normal range of motion, reducing any impediment on the user and allowing flexion, extension, lateral bending, and rotation of the neck or back of the user to be preserved. Some of these movements (e.g. flexion and extension of the neck) are associated with a coupled translational and/or rotational movement; therefore, in some example embodiments the design of the system (i.e. length of pillars, telescoping and/or pistoning and/or swiveling and/or rotating mechanism) will accommodate for full or nearly full range of motion for the user when the immobilization device is not activated. In some example embodiments, the system's design (convex and concave surfaces of the segments that comprise the pillars, surfaces with appropriate coefficient of friction, length of pillars) permit physiologic motion by virtue of intersegment motion when in the system is not activated (i.e. flexion, extension, rotation, and lateral bending, as well coupled motions).

One advantage of the design examples is increased mobility by allowing the cranial end of a pillar to telescope, piston, swiveling, rotate and/or slide in special receptors in the superior, or cranial, attachment. In this example embodiment, the upper end of the pillar may be wedge shaped, or another shape. Below the wedge shaped end of the pillar are two sliding cylindrical or spherical rollers, which are normally in the free moving position. When the system activates, a sudden tightening force is applied to the wire or cable that is transmitted all the way up to its superior end. The sudden acceleration of the wedge shaped end will exert a force to the cylindrical rolls that its direction forms an angle to the tightening axis. This force will cause the outward movement of the cylindrical rolls and then the rolls will engage to the locking recesses inside the receptors. The engagement of the rolls to the locking recesses stabilizes the cranial end of the pillar in relation to the receptor.

In some example embodiments, the pillars will attach to the helmet. The lower ends of the pillars may telescope and/or piston and/or swivel and/or rotate within the vest housing apparatus. This will allow for the physiologic range of motion to be preserved by the user. Similarly, if the lower back spine is protected, then the upper or lowers ends of the pillars would be able to telescope and/or piston and/or swivel and/or rotate within an appropriately designed housing to allow for physiologic motion.

In some example embodiments, it is desirable at times (e.g. non-combat situations, non-performance situations) to not have the pillar attached to the helmet or to the pelvic harness. The helmet articulation site can be detached by the user and stowed on the shoulder strap portion of the user's vest. Similarly, the user can easily reattach the pillars to the helmet during necessary instances. The lower pillars can similarly be detached by the user from the pelvic harness and then stowed onto a portion of the vest. Similarly, the user can easily reattach the pillars to the harness during necessary instances.

In some example embodiments, the system will be able to detect the position of the protected body part and adjust the degree of activation, and thus tightening, accordingly. In this way, the system will prevent non-physiologic recoil of a body part during activation. For example, in the case of the system being used to protect the head and neck (i.e. cervical and upper thoracic spine), if the system is activated with the neck flexed, it will lock in that position or in a similar position. This will prevent sudden, and possibly unwanted recoil of the head. This is an important part of the locking mechanism design. This "proprioceptive" property of the system (i.e. detection of body position prior to activation) allows the locking mechanism to tighten the pillars only to the appropriate degree. This locking mechanism is intrinsic to the housing apparatus, which can be built into a vest, pelvic apparatus, or can be made a component of an exoskeleton. Such rigidity of the system during activation can occur by several mechanisms. Examples include, but are not limited to: 1) the segments of the pillars forcibly pushed and locked into one another over the wire or cable; 2) translation of the wire or cable; or 3) both 1 and 2. By utilizing both the segments of the pillars forcibly pushed and locked into another over the wire or cable and translation of the wire or cable, rigidity to the system can occur with little to no recoil (i.e. of the head, for example).

In some embodiments, this device can be coupled with an exoskeleton system for use in the civilian or military contexts. In these cases, the housing apparatus for the pillars would be made intrinsic to the exoskeleton rather than into the vest or pelvic apparatus as described herein previously.

EXAMPLE APPLICATIONS

Some example embodiments of the immobilization system describe can used to prevent injury to airplane pilots. For example, ejection from a cockpit exerts significant vertical acceleration forces on fighter pilots, and shear forces resultant from the ejection at high velocity. A current trend is to incorporate additional helmet mounted systems, such as helmet-mounted displays; this trend increases the weight of the helmet and the forces exerted to the cervical spine during ejection. The proposed system can be used in this application and it can provide cervical spine protection during the fighter pilot ejection. In addition to the ejection forces, the fighter pilots are also subjected to high acceleration forces during air fights. The system can be used in this application and protect the head, neck and spine of the pilots when an excessive range of motion is detected. A different activating mechanism may be used in this application, because a repetitive activation will be needed, while the need for a very short activation time is not as essential as in other applications. The immobilization system can also protect airplane or helicopter crew and passengers from crash landings.

An additional example embodiment of the immobilization system protects combat soldiers from arms fire and explosions. For example, when a bullet strikes the head of a person there are two mechanisms that can cause brain damage. Firstly, it is the direct injury by the penetration of the skull. However, since lighter and stronger materials are being developed, a protective plate that can resist the penetration of a bullet is now feasible. If the plate stops the penetration of the skull by a bullet, there is a second mechanism that can cause brain damage through the sudden acceleration of the head caused by the bullet. The incoming bullet has marked momentum and kinetic injury and once it strikes the helmet, according to the law of conservation of momentum, a sudden acceleration to the head will ensue. The terminal velocity of the head/plate relates to the mass. The proposed application will connect the helmet/head to the rest of the body, significantly increasing the mass that the bullet hits and therefore decreasing the terminal velocity and the acceleration forces transmitted to the brain. The, gyroscope, or similar mechanical, electric, and/or magnetic sensor will cause activation and, in turn, will stabilize not only cervical spine, but also the head. The activation can be achieved either by an accelerometer sensor or a direct activation by the incoming bullet of a coiled detonation cord placed in front of the head protective plate.

Another important combat application pertains to exposure to blasts. Spinal injuries and traumatic brain injuries can result from either sudden acceleration (i.e. due to blast pressure wave), or from sudden deceleration (e.g. vehicle in collision) of the head or body resulting in brain and/or spinal cord and/or spinal column and/or nerve injury. The system is designed to activate with the described mechanism under such situations created by blasts, and to protect the user of this device from injury. The immobilization system can be used in these applications to protect the individual from spine injuries during impact, while allowing for a full range of motion of the spine at the inactivated state of the device. In certain example embodiments, the immobilization system will interface with the vehicle that has an accelerometer or other device to detect the acceleration/deceleration/hazardous changes to angular velocity, yaw and/or pitch caused by the blast wave or vehicular accident. The accelerometer or other motion, position or impact sensor sends a signal to the immobilization system(s) worn by the user(s) to activate. This allows for an early activation of the immobilization system, prior to the acceleration/deceleration effects reaching the user of the immobilization device. Some newer military vehicle concepts describe the use of rapid evasive maneuvers from the vehicle in order to avoid incoming fire. The immobilization system could prevent injuries during these evasive maneuvers. The activation of the immobilization system in this embodiment can be gradual to mitigate the acceleration forces transmitted to the brain and spine.

In another example embodiment, the immobilization system can provide head support for travelers in the sitting position. Again, since rapid activation is not necessary a manual tightening system can be utilized. Since the anticipated forces are small, the system can be built from cheaper material with less stiffness.

The immobilization device can have a caudal extension, which can be a few centimeters long, extending down approximately to the tip of the coccyx, rigid and connected to the caudal end of the pillars and the belt. The caudal extension can be connected to a receptor in the seat in the vehicle the user is traveling in and in this case the immobilization system may offer an immobilization of the person to the seat, and may negate the need for safety belts. In such a case, the person would have greater mobility compared with using the safety belt, while enjoying a greater degree of protection when the immobilization system is activated. The caudal extension can have a "T" configuration, but a person of ordinary skill in the art would understand that a number of geometries are possible based on the anticipated application. For example, if the caudal extension is intended to be inserted in a receptor in a seat, the caudal extension can have a tongue shape commonly used with seat belts to be inserted into a buckle.

In a further example embodiment, the immobilization system can be used by those skiing, snowboarding, rock climbing or other activities, such as "extreme sports", putting the user at risk of sudden accelerations/decelerations or harmful motion or impact through falling unsafe distances, or by being hit by falling debris.

BRIEF DESCRIPTION OF THE DRAWINGS

A better understanding of the present invention can be obtained from the following detailed description in conjunction with the following drawings, in which:

FIGS. 3A and 3B depict detailed views of an example embodiment of a segment for use in an immobilization device.

DETAILED DESCRIPTION OF THE PRESENT INVENTION

Figure 1:
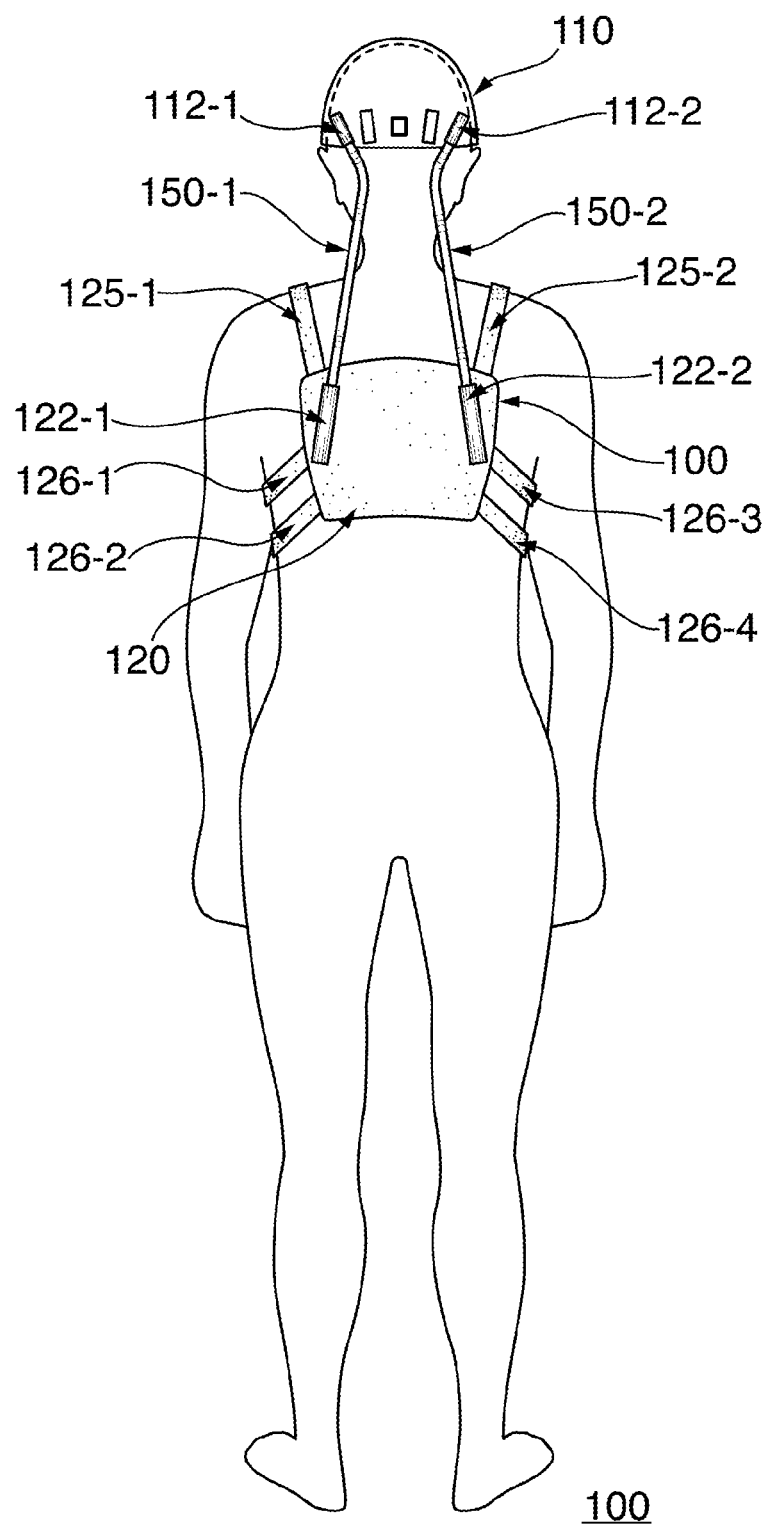
FIG. 1 depicts an example embodiment of an immobilization device with a vest.

FIG. 1 depicts an example embodiment of an immobilization device 100. The immobilization device 100 includes a helmet 110, a vest 120 and pillars 150-1 and 150-2. The helmet 110 includes helmet attachment points 112-1 and 112-2. The vest 120 includes attachment points 122-1 and 122-2, shoulder straps 125-1 and 125-2, and chest straps 126-1, 126-2, 126-3 and 126-4. The helmet 110 attaches to the vest 120 with pillars 150-1 and 150-2.

The immobilization device 100 is preferably made of lightweight materials, such as lightweight metals, fiberglass, composites or plastics. The pillars 150-1 and 150-2 attach to the helmet 110 at helmet attachment points 112-1 and 112-2, respectively. The pillars 150-1 and 150-2 extend from the helmet 110 and connect to the vest 120 at the vest attachment points 122-1 and 122-2. In the preferred embodiment, the vest 120 will be at or below the thoracic spine to increase the effectiveness of the immobilization device 100, although this is not necessary. The helmet 110 and vest 120 can be specially designed as part of the immobilization device 100, or in some example embodiments, can be an existing helmet and vest retrofitted with attachment points to connect to the pillars 150-1 and 150-2. For example, the helmet and vests used in the military can be retrofitted to be used as the helmet 110 and vest 120. In some example embodiments, the helmet 110 can be an existing helmet (e.g. motorcycle rider, fighter pilot, combat). The vest 120 can be an existing harness, vest or a new design specifically for this device. Preferably, the vest 120 has a wide rigid surface that disseminates forces to the surface of the thorax of the user. Preferably, the vest 120 should also attach circumferentially on the chest. In the example embodiment depicted in FIG. 1, the vest 120 includes chest straps 126-1, 126-2, 126-3 and 126-4 to secure the vest 120 to the user. The vest 120 further includes shoulder straps 125-1 and 125-2 to further secure the vest 120 to the user. The chest straps 126-1, 126-2, 126-3 and 126-4 and shoulder straps 125-1 and 125-2 may be of any material known and convenient and can be secured and/or tightened to the user via conventional means such as latches, buckles, or hook-and-loop fastener depending on the application.

The pillars 150-1 and 150-2 are flexible under normal conditions, referred to as the "inactivated" state for the pillars. The pillars 150-1 and 150-2 can also be in an "activated" state, where the pillars become rigid by a rapid tightening of an internal wire or cable that stabilizes multiple segments that collectively form the pillars 150-1 and 150-2. The segments can have a variety of shapes, have a lumen and are preferably durable to large forces or heat and made of a strong and lightweight material. In some example embodiments, one end of the segment is convex and the other end of the segment is concave. Each end of a segment articulates with the respective end of the adjacent segment (i.e. concave ends articulate with convex ones). Preferably, an inelastic wire or cable of sufficient strength properties runs in the lumen of the segments lumen. When the immobilization device 100 is in activated state, the pillars 150-1 and 150-2 become rigid as interlocking segments key into each other as the wire or cable is tightened or the segments are tightened together through a locking mechanism pushing the first segment in the chain forward. In some example embodiments and applications, particularly when immobilization is required as rapidly as possible, a pyrotechnic, compressed gas, magnetic, and/or electric mechanism or other mechanism known and convenient provides the necessary tightening force. The pyrotechnic, compressed gas, magnetic, and/or electric mechanism, in turn, activates a global device tightening and locking mechanism that confers rigidity to the head and upper spine through the helmet 110 and vest 120. In some example embodiments, the tightening of the wire or cable can be performed through the use of an electric motor or spring system embedded in the helmet 110 and/or vest 120. In other example embodiments, one segment will be shifted towards the other segments causing all the segments to compress together. In this example embodiment, the segment can be shifted with a spring, a compressed gas or explosives, or other mechanism capable of generating the desire force. The segment will then be locked in place in the shifted position. Example of the segments able to be used in immobilization device 100 can be seen in references to FIGS. 3A, 3B and 4. Examples of the how the segments can be used to activate the pillars 150-1 and 150-2 in immobilization device 100 can be seen in reference to FIGS. 5A, 5B, 10A, 10B and 10C. Examples of the locking mechanisms that can be used in pillars 150-1 and 150-2 can be seen in reference to FIGS. 6, 7, 8A and 8B.

The pillars 150-1 and 150-2 include an optional sleeve covering the segments, which can be of any flexible material known and convenient such as nylon, plastic, or fabric. The pillars 150-1 and 150-2 may be enclosed in a flexible sleeve to protect them from corrosion or wear, and help prevent binding with neighboring materials. In some example embodiments, the sleeve may be made of cloth, soft plastic, rubber, nylon, leather, any combination of these materials, or any other material known and convenient to a person of skill in the art.

While FIG. 1 depicts the immobilization device 100 with two pillars, a person of ordinary skill in the art would recognize that a different number of pillars could be used. For example, in some example embodiments a single pillar may be sufficient. While in additional example embodiments, three or more pillars may be used for increased support. The number and the exact shape of the pillars will depend on the specific application. In applications where the user will be in the upright position, two pillars that run along the spine on the back of the user may provide adequate protection. In applications where the user is seated, then the pillars might run on the front of his body as well. The diameter and the number of the pillars used, as well as their location will depend on the overall stabilization required for the specific application. Furthermore, the number of segments used in a pillar will vary on the application, the length of the pillar, and the length of the segments. Preferably, enough segments will be used that when the wire or cable running through them contracts and the device activates, the segments lock together, but when inactivated are spaced enough apart so the segments are able to articulate.

The helmet attachment points 112-1 and 112-2 may attach the pillars 150-1 and 150-2 to the helmet 110 by a plain fixed attachment. The harness attachment points 122-1 and 122-2 may attach the pillars 150-1 and 150-2 to the vest 120 by a plain cylindrical, hollow connector, by rigidly fixing one or more segments to the vest 120. In some example embodiments, to accommodate neck or back flexion and extension the immobilization device 100 includes a telescoping mechanism in the helmet 110 or vest 120, permitting a greater range of motion. For example, the telescoping mechanism allows a user a greater range of motion for looking up at the sky; bending forward to tie one's shoes. The telescoping mechanism acts as a sheath through which the pillars 150-1 and 150-2 pass. The telescoping mechanism is shown in greater detail in reference to FIG. 8. In some example embodiments, the telescoping, pistoning, swiveling and/or rotating mechanism are built into the system housing located in the vest 120.

The immobilization device 100 may be activated in several ways. In some example embodiments, the electrical system of an aircraft, car, tank or other transportation system couple to immobilization device 100. The immobilization device 100 can be coupled to the electric system of a transportation system in any way known and convenient, such as through a wired data port connection like USB or wirelessly through a connection like Wi-Fi or Blue Tooth. In these cases, the transportation system can communicate with the immobilization device 100 and indicate if activation is necessary or appropriate. The control system can also provide information on the strength required in activation, allowing for more or less rigidity in the pillars depending on the detected conditions. For example, if a pilot is required to eject from an aircraft, the control system could communicate to or with the immobilization system 100 to activate and thereby stabilize the user during turbulence, a crash or harmful or unpleasant forces. In some further example embodiments, an accelerometer and/or gyroscope may be embedded in the immobilization device 100. When a sudden acceleration, deceleration or change in orientation is detected the immobilization device 100 may be activated. The accelerometer and/or gyroscope can also provide information on the strength required in activation, or provide data to a processor in the immobilization device able to calculate the appropriate response, and allowing for more or less rigidity in the pillars depending on the detected conditions. In some alternative embodiments, a combination of accelerometer and gyroscope is used to detect acceleration and orientation changes indicating the immobilization device 100 should be activated. Furthermore, the immobilization device 100 may include a manual activation switch or button, allowing the wearer to activate the immobilization device 100.

In some example embodiments of the immobilization device, an accelerometer is located in the helmet or at the cranial end of pillars 150-1 or 150-2 to sense any sudden acceleration or deceleration of the head. Moreover, in applications where sudden acceleration or deceleration is anticipated first in the thoracic or lumbar spine, then one or more accelerometers can also be placed in these locations (E.g. in the vest 120). In some example embodiments, the immobilization device includes a processor able to read various acceleration inputs and determine if activation of the immobilization device 100 is necessary or appropriate. The immobilization device can include a processor for determining the correct response based on the various acceleration or orientation inputs. This information can also be stored for later use on memory included in the immobilization device 100 to later reconstruct a timeline of events, similar to a "black box" on a commercial airliner.

In additional example embodiments, if there is a need to limit the electronics contained within immobilization device 100, then a mechanical or an electrical activation mechanism can be used. A short flexible cord suspends a sphere of weight. The sphere is connected through the cord to a pin that holds a firing pin. The pin-firing pin assembly attaches to the body part (e.g. head), whose acceleration will activate the device. An acceleration of sufficient force to the protected body part moves the pin/firing pin. When the cord of the free hanging sphere comes under tension, then the cord will exert a pulling force on the pin that is holding the firing pin. The pin is pulled out and the firing pin will be released. The firing pin will either hit a detonation cord to activate the system or it will close an electrical circuit, causing an electrical activation of the system.

In some example embodiments of immobilization device 100, particularly versions intended to protect the head from the impact of a bullet, an extremely rapid activation is required and activation of the immobilization device 100 is achieved by placing a coiled lightweight detonation cord in the head protection plate. The incoming bullet activates the detonation cord before reaching the protection plate. The detonation cord transmits the activation to the main activation pyrotechnic or compressed air charge with a speed sufficient to protect the user.

In example embodiments of immobilization device 100, particularly embodiments intended for applications for motorcycle riders, the immobilization device 100 connects to the motorcycle, or water vehicle. In the event of the user falling, this cable is pulled out and activates the system. An additional option is to have the activation of the immobilization device 100 be transmitted from a vehicle and/or computer or electrical system of the vehicle in which the user is riding. This activation can be triggered by electronic accelerometer attached to the vehicle that is designed to detect abnormal changes in direction or deceleration, or abnormal changes in direction (i.e. yaw, pitch, or roll). In the event of a collision or explosion that results in a sudden abnormal increase in yaw, pitch or roll of the vehicle, the immobilization device 100 will be activated to protect the user(s) in the vehicle. In further example embodiments, additional sensors may be used to detect changes in air pressure indicative of an explosion and required activation of the immobilization device 100.

The number of pillars used (one, two, three or more) in an immobilization device, and their spatial positioning can be variable and this will be predicated on the demands of the user and anticipated environmental situations (e.g. military combat, extreme sporting). The optimal positioning and number will confer maximal achievable resistance to motion in all planes.

Figure 2:
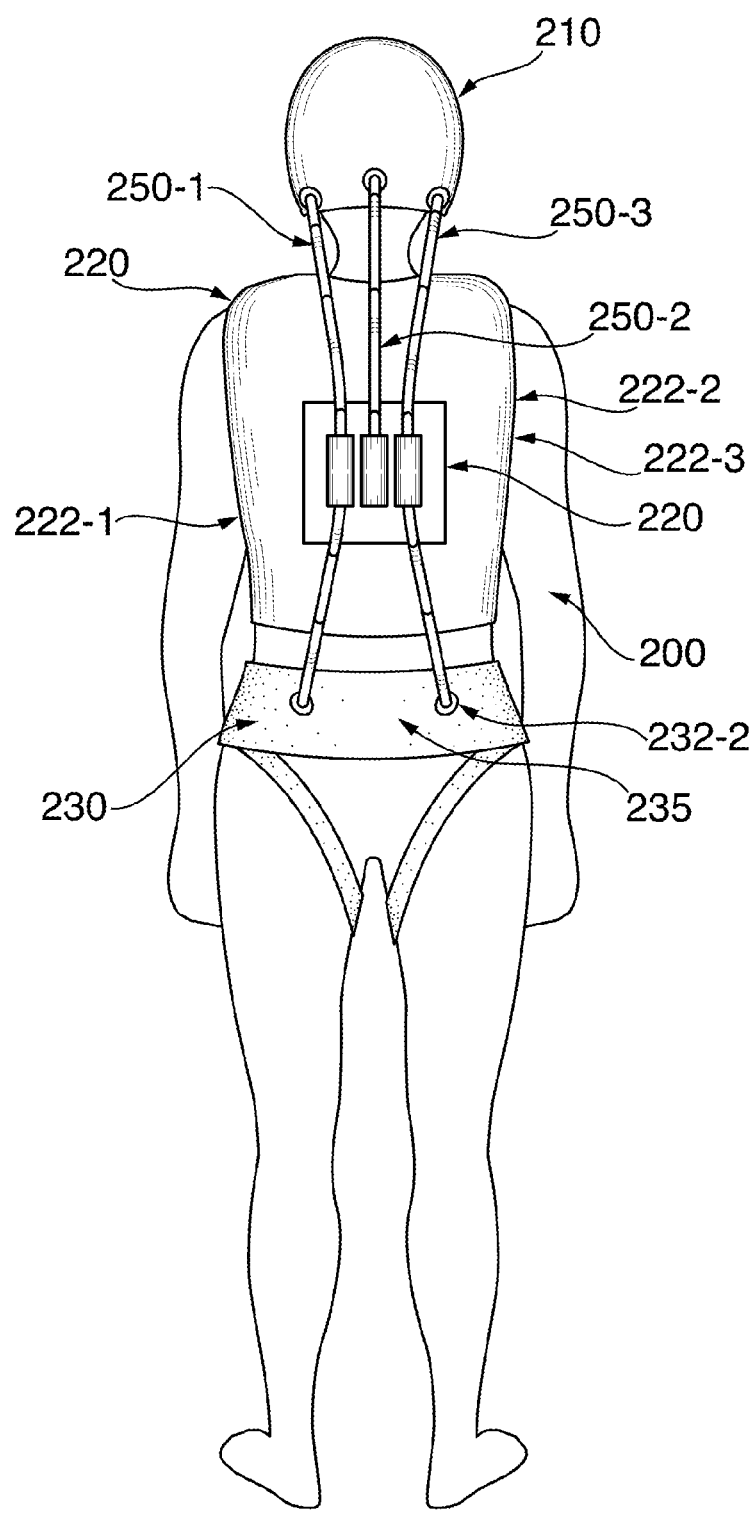
FIG. 2 depicts an example embodiment of an immobilization device with a vest and a belt.

FIG. 2 depicts an example embodiment of an immobilization device 200. The immobilization device 200 includes a helmet 210, a harness 220, a belt 230 and pillars 250-1, 250-2 and 250-3. The immobilization device 200 is similar in most respects to the immobilization device 200 depicted in FIG. 1, however the pillars 250-1 and 250-3 reach pelvis and attach to belt 230. Immobilization device 200 also includes a third pillar 250-2 that attaches to the harness 220. The pillar 250-2 can also extend to the harness in some embodiments, or that pillars 250-1 and 250-3 may attach only to the harness 220, while the pillar 250-2 attaches to the belt 230, depending on the requirements of the particular application. Examples of segments that can be used to activate the pillars 250-1 and 250-2 in immobilization device 200 can be seen in reference to FIGS. 5A, 5B, 10A, 10B and 10C. Examples of the locking mechanisms that can be used in pillars 250-1 and 250-2 can be seen in reference to FIGS. 6, 7, 8A and 8B. The immobilization device 200 can be activated as described in reference to FIG. 1.

In some example embodiments, immobilization device 200 will have a caudal extension distal in the belt 230. An example of the caudal extension is described in greater detail in reference to FIG. 9. The attachment points to the vest 222-1, 222-2 and 222-3 might be hollow tubes that would allow the pillars to slide through. In this case the activation mechanisms are located in the helmet and/or belt. Alternatively, the attachment points 222-1, 222-2 and 222-3 might be anchoring points for the pillars and contain the activation mechanisms.

The immobilization device 200 includes a belt 230 that can have a rigid surface at the site of the pillars connection to disseminate force over a larger surface. Thigh straps can offer added stability to the system by creating an additional point of stabilization.

Figure 11:
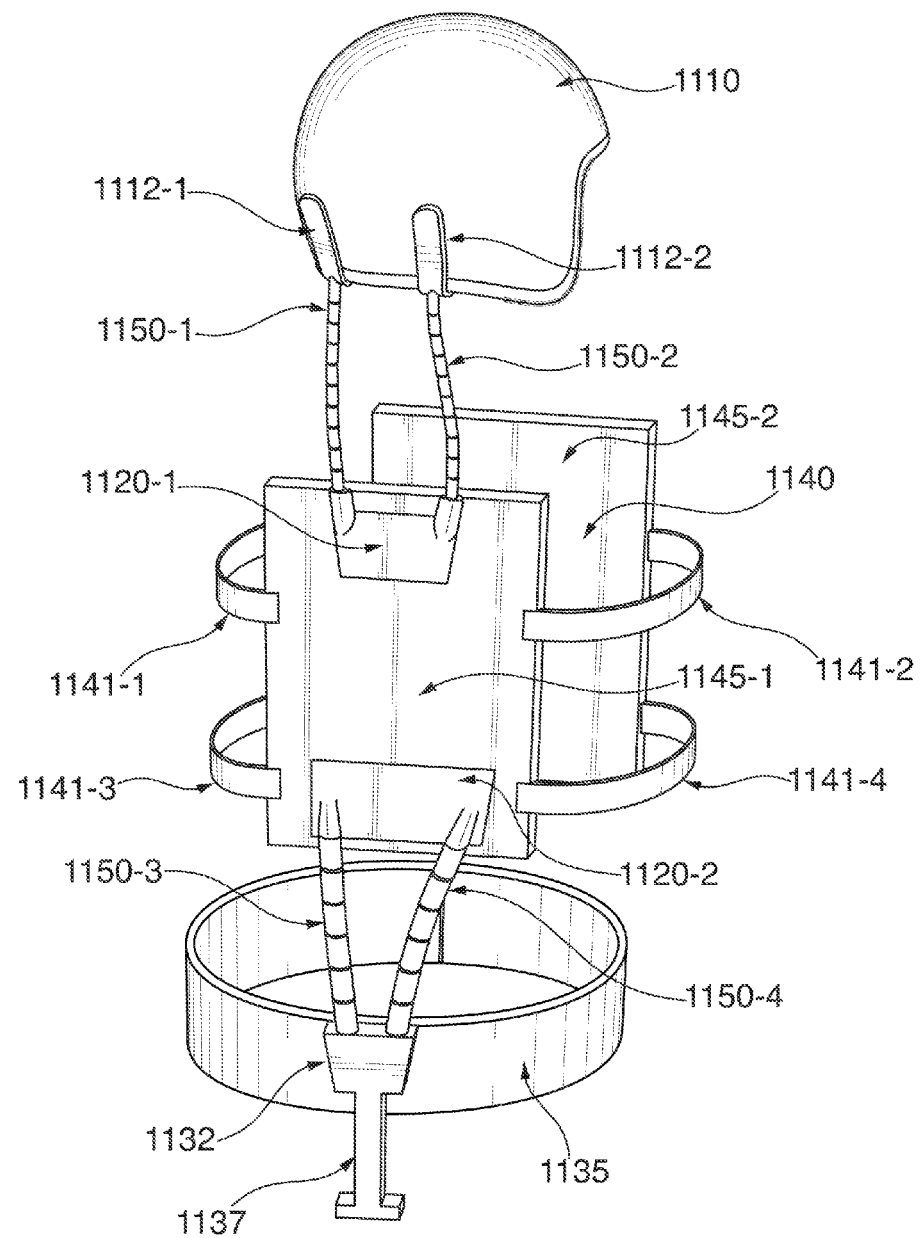
FIG. 11 depicts an example embodiment of an immobilization device with a vest, a belt and caudal extension, and with segments exposed.

FIGS. 3A and 3B depict two views of a segment 300 for use as a modular component in the pillar of a head and spine immobilization device as depicted in FIGS. 1, 2 and 11. The segment 300 is cylindrical in shape with a convex end 310, a concave end 320 and a hollow lumen 330 centrally located on the cross section of the segment 300 and running along the longitudinal axis of the segment 300. Preferably, the segment 300 is made of a lightweight, durable and stiff material such as carbon fiber, ceramics, metal, metallic alloy or plastic. Furthermore, the segment 300 is preferably heat resistant. The diameter of the segment 300 depends on the level of stabilization required for the immobilization device the segment 300 is integrated into, as a greater diameter will typically be able to withstand greater forces. The length of the segment 300 may also vary between the intended purpose of the immobilization device, and the size of the intended user of the immobilization device, as smaller users may require smaller segments. The example embodiment depicted in FIG. 3A includes a wire 340 running through the lumen 330 of the segment 300. The lumen 330 is a circular hole running the length of the segment 300. However, a person of ordinary skill in the art would recognize the that other shapes may be used. The convex end 310 is spherical and the concave end 320 with a spherical indentation. Again, a person of ordinary skill in the art would recognize that other geometries can be used, such as oval, triangular, square or rectangular. The lumen 330 has a circular opening on both the convex end 310 and concave end 320 of the segment 300. The diameter of the lumen 330 will be sufficient to allow a wire to run through the segment 300 without impedance and minimal friction. However, a person of ordinary skill in the art would recognize that the lumen 330 may have alternative geometries based on its use and the wire intended to run the length of the segment 300. FIG. 3B further shows the spherical outer surface 380 of the segment 300.

While FIGS. 3A and 3B depict the segment 300 having a cylindrical shape, a person of ordinary skill in the art would recognize that different shapes are possible. For example, the cross section of the segment 300 may be oval shaped rather than circular when viewed top down as shown in FIG. 3B, allowing a thinner cross section in one dimension. The cross section of the segment 300 may be triangular, square, rectangular, or any other shape known and convenient.

Figure 4:
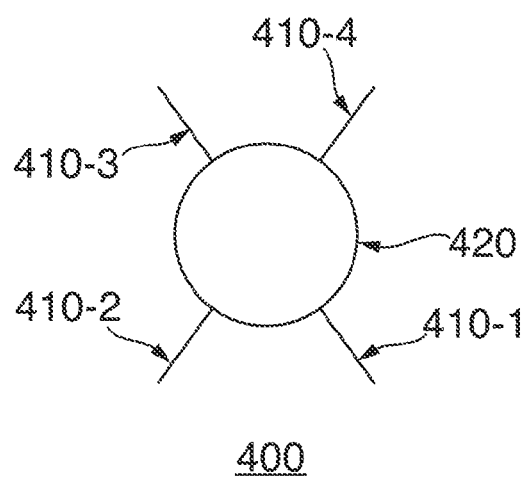
FIG. 4 depicts a detailed view of an example embodiment of a segment with fins for use in an immobilization device.

FIG. 4 depicts additional example embodiment of segment 400 designed with fins 410-1, 410-2, 410-3 and 410-4, respectively, geometrically positioned to confer maximal ergonomic suitability for the segment 400, as well as necessary stiffness or strength, minimizing mass, and weight and for use as a modular component in the pillar of a head and spine immobilization device as depicted in FIGS. 1, 2 and 11. The segment 400 is similar to segment 300 described in reference to FIG. 2. For example, the segment 400 has a similar concave end and concave end, a hollow lumen running along the longitudinal length of the segment 400 and may be made of the same materials. Segment 400 also includes fins 410-1, 410-2, 410-3 and 410-4 that run the length of the segment and convey additional stiffness of a larger diameter segment at a fraction of the weight. The fins 410-1, 410-2, 410-3 and 410-4 will typically be made of the same lightweight and durable material as the segment 400.

Figure 5A:
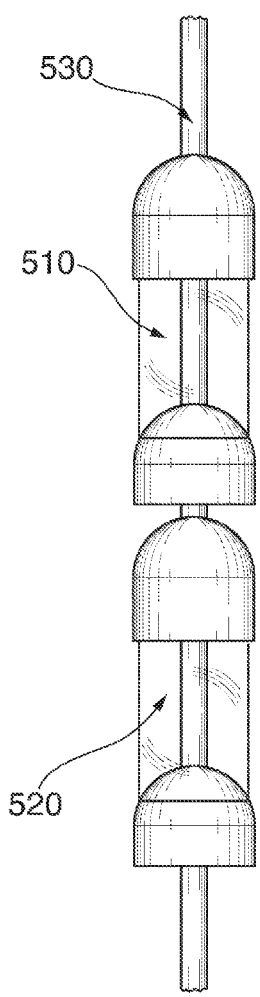
FIGS. 5A and 5B depict detailed views of example embodiment of segments for use in an immobilization device and in activated and inactivated states.
Figure 5B:
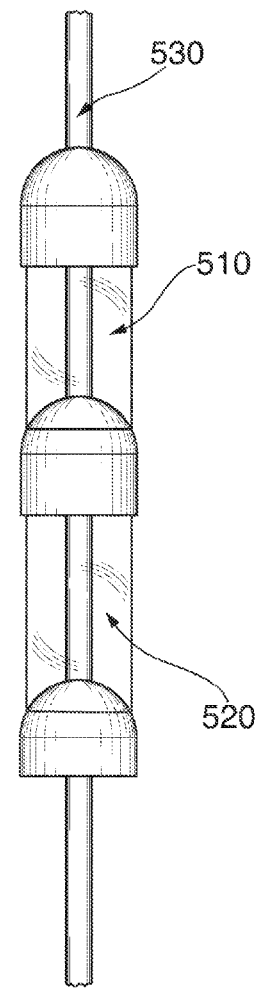

FIGS. 5A and 5B depict a detailed view of segments 510 and 520 in inactivated and activated states. The segments 510 and 520 are similar to the segments described in FIGS. 3A, 3B, 4, 10A, 10B and 10C and are typically used in the pillars described in reference to FIGS. 1, 2 and 11, which consist of the segments and the cable 530 that runs through the lumen of the segments 510 and 520. When the segments 510 and 520 are in the non-activated configurations depicted in FIG. 5A, the pillar is flexible and able to bend. FIG. 5B depicts the segments in the activated configuration; the pillars confer rigidity, and thus resistance motion of the head and spine. In FIG. 5B, the segments 510 and 520 are keyed together by restricting the wire 530 running through the lumen of the segments 510 and 520, subsequently the segments are pushed and/or translated together. There are several options for activation of immobilization device. For example, several wire or cable locking mechanisms may be used, as described in FIGS. 6, 7, 8A and 8B.

Furthermore, FIGS. 5A and 5B are illustrative only and multiple segments may be used, all of which will be keyed together, concave end of one segment keyed into the convex end of the next segment when the pillars are activated. Typically, at the attachment points of the immobilization device, such as shown in FIGS. 1, 2 and 11, special terminating segments are used and affixed to the attachment points. In particular, the most proximal segment to the attachment point is fixed to the attachment point and—if there is one at this attachment point—the wire tightening mechanism. The terminating segments can be glued, welded, screwed, or bolted to the attachment point, or affixed using any other method known and convenient.

Figure 6:
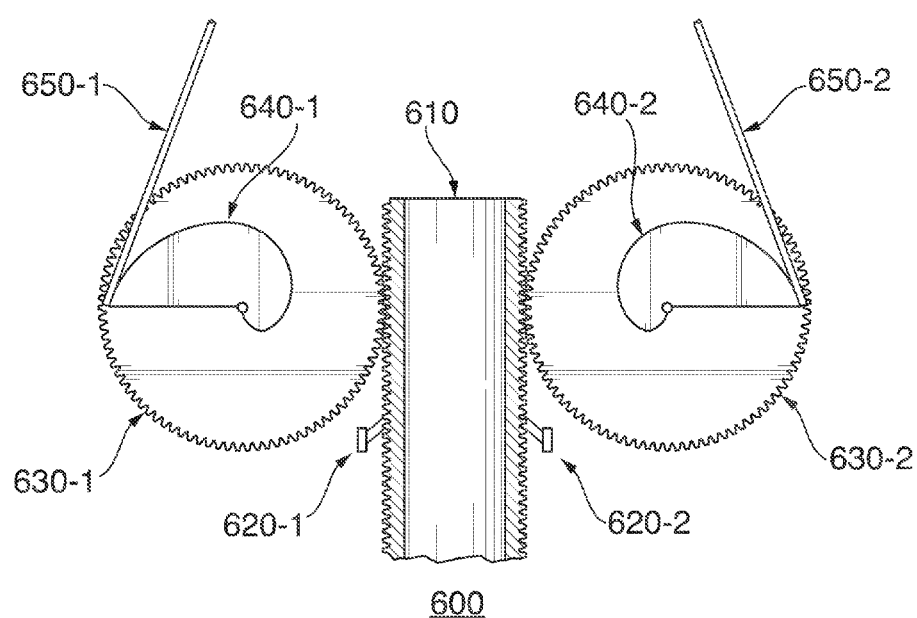
FIG. 6 depicts a detailed view of an example embodiment of a gear locking mechanism for pillars in an immobilization device.

FIG. 6 depicts a detailed view of an example embodiment of a gear locking mechanism 600 for pillars in an immobilization device. One of the possible tightening mechanisms (regardless of the energy source e.g. compressed gas, pyrotechnics) for use in an immobilization device will tighten the wire/cable by a piston 610 an engaging a locking mechanisms 620-1 and 620-2 that will prevent the backwards motion and will lock the piston 610 in place. The piston 610 rotates two gears 630-1 and 630-2 using a rack and pinion mechanism. The gears 630-1 and 630-2 include teeth that interlock with teeth on the piston 610 and when the piston 610 is moved gears 630-1 and 630-2 rotate. Each of the gears 630-1 and 630-2 are attached to coaxial gears 640-1 and 640-2, respectively, with the coaxial gears 640-1 and 640-2 having a progressively smaller diameter.

Gear locking mechanism 600 can be used to activate the pillars shown in FIGS. 1, 2 and 11 and can be located in the vest, helmet, belt or any other location known and convenient. To activate, a force will be asserted in the piston 610, causing the piston 610 to shift upward, rotating the gears 630-1 and 630-2, and by transference, the coaxial gears 640-1 and 640-2. The coaxial gears 640-1 and 640-2 work as reels to coil the wires 650-1 and 650-2, respectively, causing the wires 650-1 and 650-2 to tighten. The differential diameter of coaxial gears 640-1 and 640-2 offers a rapid initial tightening of the slack wire and at the end of tightening the smaller diameter will lead to a tightening with greater torque, achieving a high degree of tension on the wires 650-1 and 650-2. This mechanism will tighten the wire and to cause the activation of the pillars described in FIGS. 1 and 2, through the locking of the segments described in FIGS. 5A and 5B.

Figure 7:
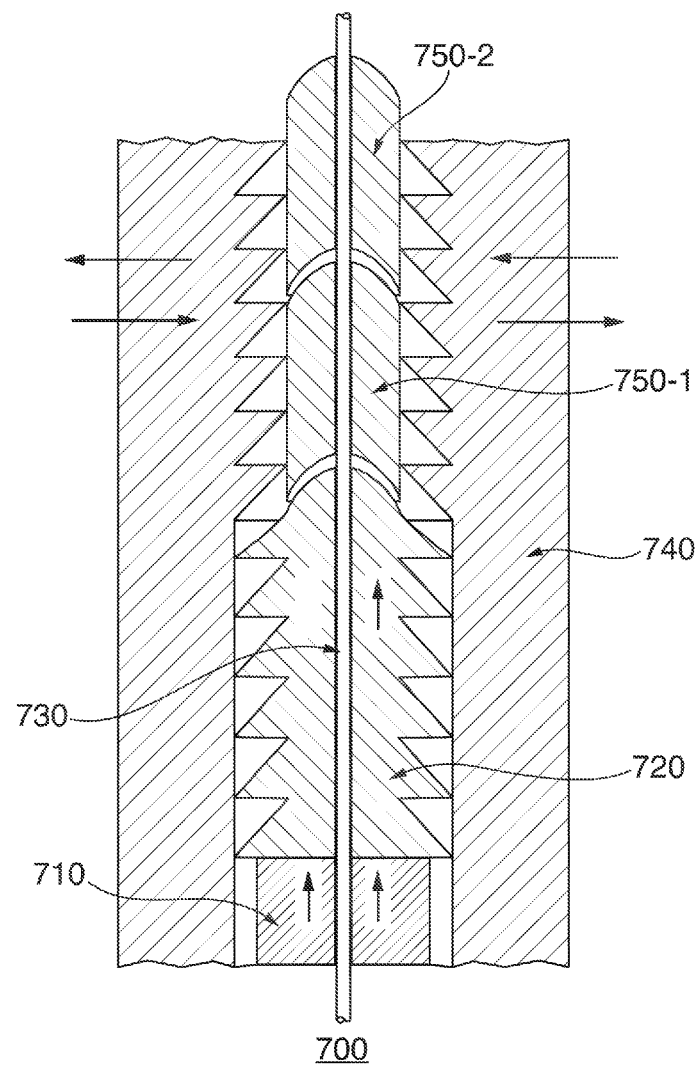
FIG. 7 depicts a detailed view of an example embodiment of a locking mechanism for pillars in an immobilization device.

FIG. 7 depicts a detailed view of an example embodiment of a piston and ratchet locking mechanism 700 for pillars in an immobilization device. Locking mechanism 700 includes a chamber 710, locking piston 720, wire or cable 730, interlocking peripheral component 740 and segments 750-1 and 750-2. Locking mechanism 700 may be activated by compressed gas, spring or pyrotechnic charge within a chamber 710 that when activated drives the locking piston 720 into the concave section of the segment 750-1 which in turn keys into segment 750-2. In some example embodiments, a piston pushes into the convex portion of a segment (depending on the direction of the pillar).

The locking piston 720 engages a ratcheted mechanism in a forceful fashion that pushes up into segment 750-1 and locks the individual segments. This figure only shows segments 750-1 and 750-2, but typically a number of segments would be after segment 750-2, but not depicted in this figure. These segments would continue the length of a pillar, as discussed in reference to FIGS. 1, 2, 5A, 5B and 11. The interlocking peripheral component 740 of locking mechanism 700 affords elastic expansion during the ascent of the locking piston 720 in the chamber 710, and then immediate retraction to effectively lock the locking piston 720 in place with the teeth of the interlocking peripheral component 740. The interlocking peripheral component 740 may be segmented and include an elastic material and/or device (e.g. spring) to effect this type of expansion and retraction. Alternatively, the interlocking peripheral component 740 is not be segmented and instead made of a material with elastic properties to achieve this desired mechanism. Alternatively, the interlocking peripheral component 740 includes a hinged safety allowing movement only to one direction (towards tightening the pillar) and will not permit any movement to the opposite direction. The wire 730 is anchored to the interlocking peripheral component 740. The ratchet locking mechanism 700 can be used to activate the pillars shown in FIGS. 1, 2 and 11 and can be located in the vest, helmet, belt or any other location known and convenient.

An additional example embodiment, to the piston/ratchet mechanism will use the same ratchet and piston mechanism and a wire terminates into the piston. In this example embodiment, instead of pushing the segments together, upon activation of a charge, spring or compressed gas, pistons at opposite ends of the pillar move in opposite directions resulting in pillar activation, and thereby rigidity of the pillar. In some example embodiments, for example if the system is attached to the cervical spine/head, then only one piston moves upward to active the pillar. Thus, the type of locking mechanism incorporated in the user's vest will be predicated on the portion of the body targeted for protection. The ratio of allowable motion of either pillar is designed to maximize rigidity while minimizing motion and recoil of the head or back.

An additional example embodiment, the locking of the segments of the pillars is initiated in a gas chamber, located in the vest of the user, into which compressed gas is injected during system activation. This will cause a rapid rise in pressure that will push a drive piston in the desired direction. The drive piston will be solid with a central hole to accommodate the wire or cable used in the system. The drive pistons will have a several O-rings to maintain pressure within the gas chamber. A rise in pressure inside the gas chamber will push the drive pistons in the desired direction. The drive piston and the internal walls of the gas chamber will have mechanical excursion blocks to limit the movement of the drive pistons. The movement of the drive pistons, in turn, pushes the segments of the pillars in the desired direction to the desired excursion which, in turn, causes activation, or locking, of the system. Deactivation of the system can be manual or automatic. Both the latter and former will involve opening a temporarily opening a gas efflux valve to cause an efflux of the compressed gas to the environment thereby deactivating the system and conferring flexibility to the system again. The drive pistons within the gas chamber(s) may be spring loaded (not pictured) to ensure recoiling into the proper "start" position.

In some example embodiments, the fast activation or tightening mechanism for the pillars may be a pyrotechnic or a compressed gas mechanism activated by an activation mechanism. In applications where rapid activation (causing pillars to become rigid) and tightening is not necessary, then a manual-tightening device can be used, such as an electric motor. In applications where repetitive activation is needed (e.g. fighter pilot version) an electrical or hydraulic tightening system can be used.

Figure 8A:
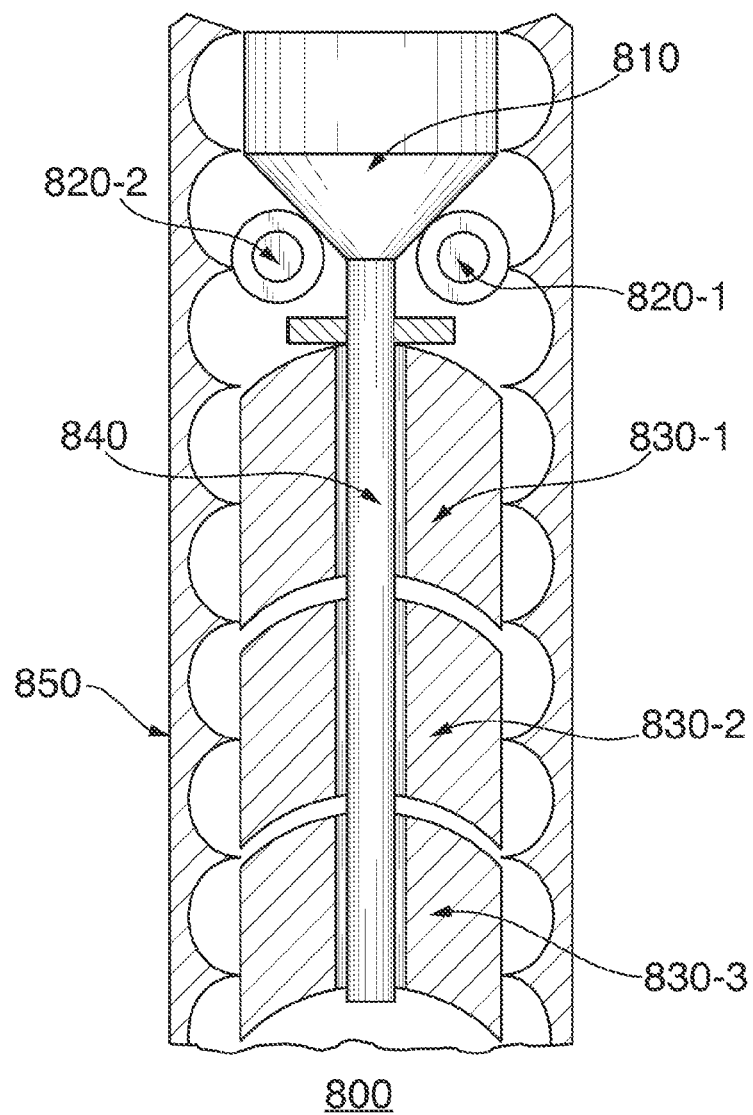
FIGS. 8A and 8B depict detailed views of example embodiments of a locking mechanism for pillars in an immobilization device utilizing a piston and ratchet locking mechanism.
Figure 8B:
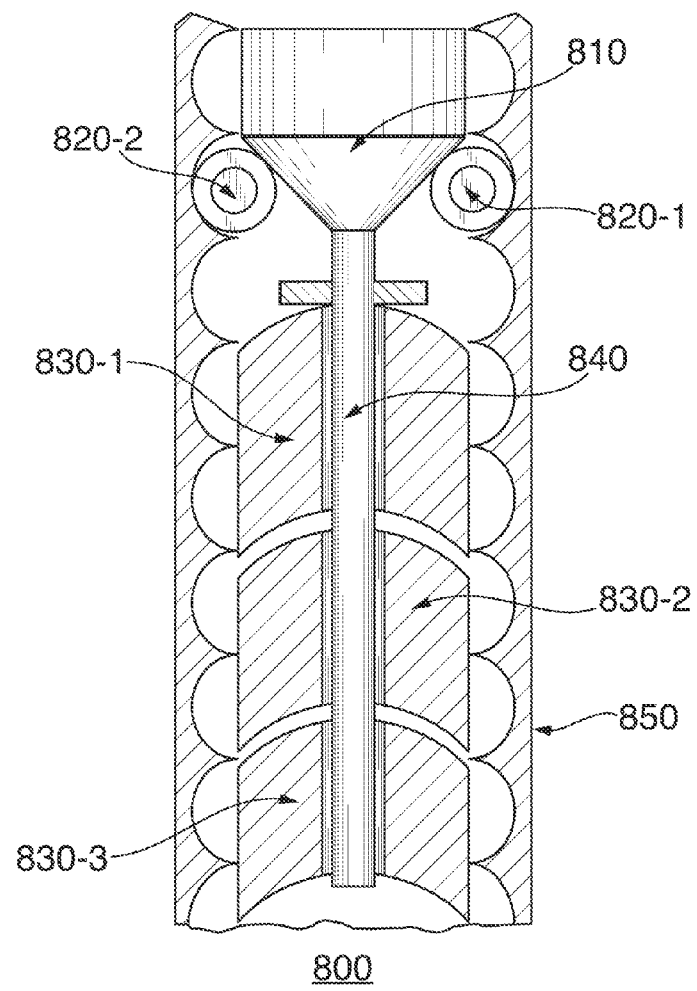

FIGS. 8A and 8B depict detailed views of example embodiments of a telescoping locking mechanism 800 for a pillar in an immobilization device utilizing a piston and ratchet locking mechanism. The locking mechanism 800 includes a wedge end piece 810, rollers 820-1 and 820-2, segments 830-1, 830-2, and 830-3, cable 840, and interlocking peripheral component 850. The telescoping locking mechanism 800 is used in a pillar connected to the cable 840 that runs inside the segments 830-1, 830-2, and 830-3. The interlocking peripheral component 850 includes ridges that are peripherally located in its inner surface creating multiple recesses. The width of the wedge end piece 810 is smaller than the distance between the tips of the ridges in the interlocking peripheral component 850 (inner diameter) to allow for the free movement of the wedge shaped end piece

810. When the locking mechanism 800 is not activated the roller 820-1 and 820-2 lie within the tips of the lateral recesses of the interlocking peripheral component 850 and allow the free movement of the wedge shaped end piece 810 in a pillar. When the system is activated, a sudden tightening force is applied to the cable 840 that is transmitted up to the cranial end of the pillar in which the locking mechanism 800 is used. The sudden acceleration of the wedge shaped end piece 810 forces the cylindrical rollers 820-1 and 820-2 in the direction the cable 840 is tightened and forms a 45-degree angle to the tightening axis of the cable 840. This force causes the outward movement of the cylindrical rollers 820-1 and 820-2 to engage with the recesses inside the interlocking peripheral component 850. The engagement of the cylindrical rollers 820-1 and 820-2 to the locking recesses of the interlocking peripheral component 850 stabilizes this way the cranial end of the pillar in relation to the receptor, when traction forces develop between the peripheral component 850 and the internal components. If the forces that develop between the peripheral component 850 and the internal components are compression forces, the stability is achieved by a short delay in the return of the rollers 820-1 and 820-2 in their inner position (the inner position normally allows free movement). This delay would allow the most cranial segment 830-1 to engage against the rollers and stop any further compression movement. The telescoping locking mechanism 800 can be used to activate the pillars shown in FIGS. 1, 2 and 11 and can be located in the vest, helmet, belt or any other location known and convenient.

Figure 9:
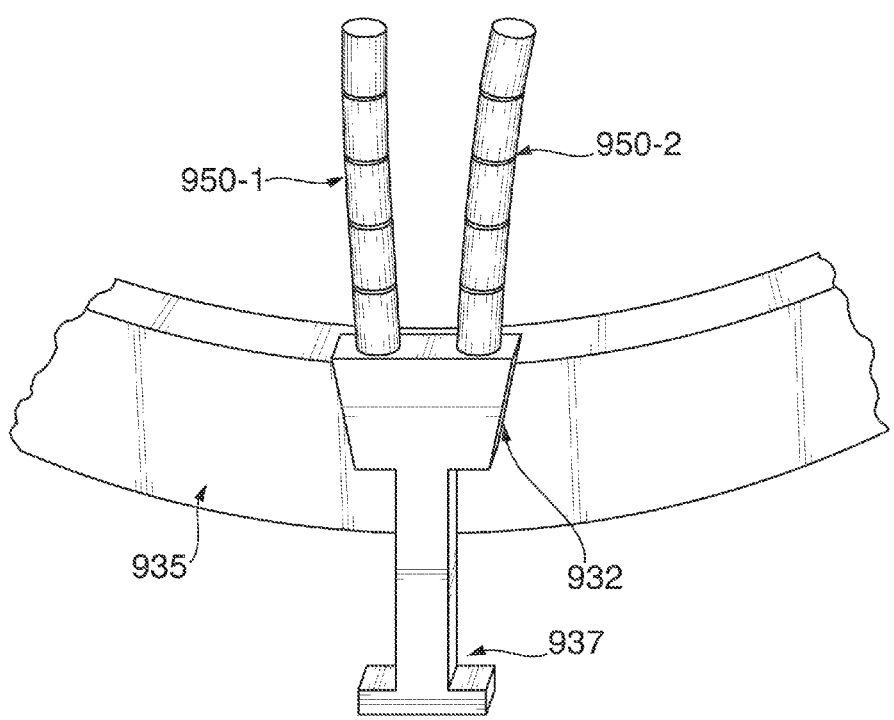
FIG. 9 depicts a caudal extension.

FIG. 9 depicts a detailed view of an immobilization device with a caudal extension 937. Typically, the caudal extension 937 will be a few centimeters long, extending down approximately to the tip of the coccyx, rigid and connected to the caudal end of the pillars 950-1 and 950-2 and the belt 935 by attachment point 932. The caudal extension 937 prevents the adverse effects or vertical acceleration (e.g. explosion underneath a vehicle). The caudal extension 937 will transfer the weight of equipment (e.g. helmet, vest) and part of the body weight directly to the seat, offloading, or splinting the immense forces from the spine and lead to injuries. The caudal extension 937 can be connected to a receptor in the seat in the vehicle the user is traveling in and in this case the immobilization system would offer an immobilization of the person to the seat, negating the need for safety belts. In such a case, the person would have greater mobility compared with using the safety belt, while enjoying a greater degree of protection when the immobilization system is activated. The caudal extension 937 is shown with a "T" configuration, but a person of ordinary skill in the art would understand that a number of geometries are possible based on the anticipated application. For example, if the caudal extension is intended to be inserted in a receptor in a seat, the caudal extension can have a tongue shape commonly used with seat belts to be inserted into a buckle.

Figure 10A:
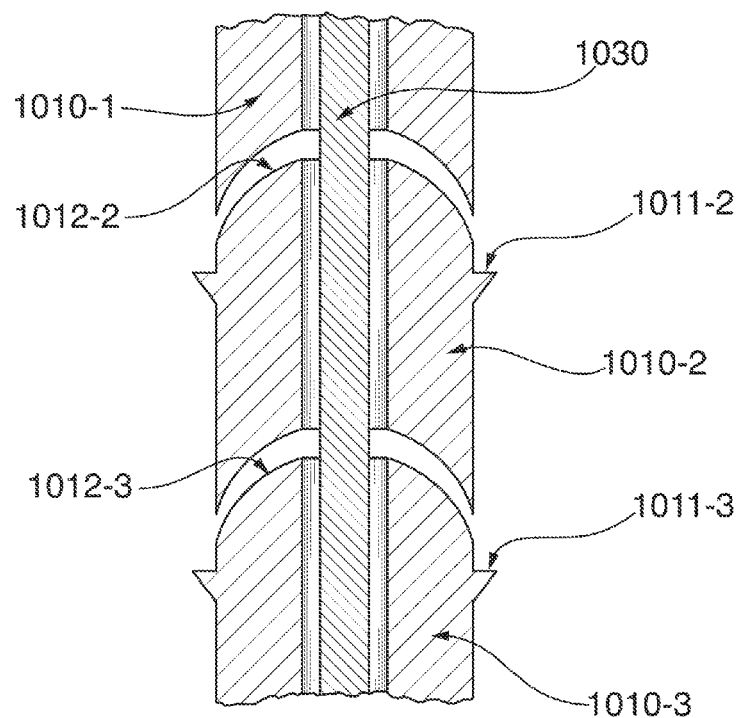
FIGS. 10A, 10B and 10C depict a detailed view of the cross section of example embodiments of segments for use in an immobilization device.

FIG. 10A depicts a detailed view of the cross section of example embodiments of segments for use in an immobilization device. The wire 1030 runs through the lumen of segments 1010-1, 1010-2 and 1010-3. Segments 1010-1, 1010-2 and 1010-3 include peripheral projections 1011-2 and 1011-3, and curved surfaces 1012-2, 1012-3 (segment 1010-1 would include a peripheral projection and a curved surface as well, but is not shown in FIG. 10A). FIG. 10A is a cross section view of the segments 1010-1, 1010-2 and 1010-3 and the Peripheral projections 1011-2 and 1011-3 would typically wrap around the entire exterior of the typically circular exterior of the segments 1010-1, 1010-2 and 1010-3. Peripheral projections 1011-2 and 1011-3 are an optional configuration of the segments 1010-1, 1010-2 and 1010-3 and prevent bending of two adjacent segments beyond a certain angle, which can be determined by the size and geometry of the peripheral projection. The exact location of the peripheral extensions 1011-2 and 1011-3 in regards to their distance from the curved surface 1012-2 and 1012-3 can be designed to limit the bending within the normal range of motion at the various spinal regions. This special design would place the peripheral projection at different distances from the convex surface at the anterior, lateral, posterior aspects of the segment, simulating the different flexion/lateral flexion/extension range of motion of the various spine regions. The peripheral projections 1011-2 and 1011-3 are shown with a straight edge and point, but other shapes, such as a rounded or semicircular projection can be used in the alternative. The peripheral extensions can serve as a fail-safe mechanism, in case the friction forces between the concave-convex ends of the segments fail to stabilize the system against severe forces.

Figure 10B:
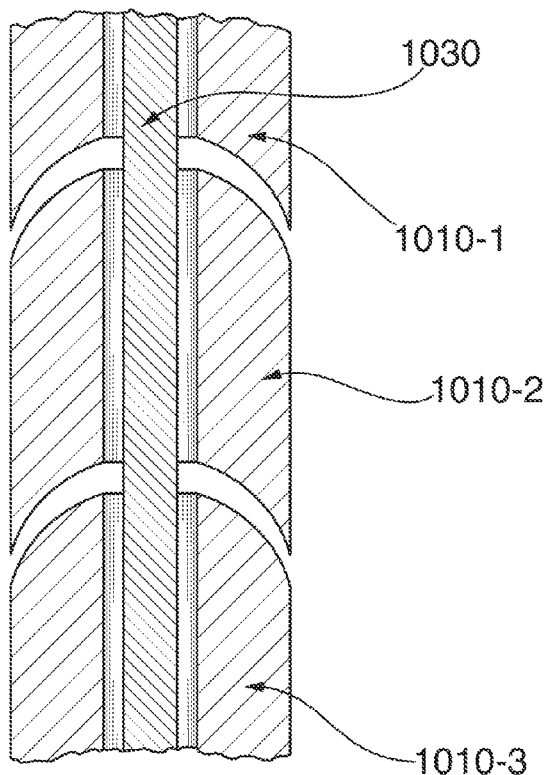

FIG. 10B depicts a detailed view of the cross section of example embodiments of segments for use in an immobilization device. The segments 1010-1, 1010-2 and 1010-3 in FIG. 10B are similar to FIG. 10A, however are shown without peripheral extensions. Segments 1010-1, 1010-2 and 1010-3 include convex and concave curved surfaces. The curved surfaces can be coat in enamel or other material to achieve optimum friction between the segments when used in an immobilization device.

Figure 10C:
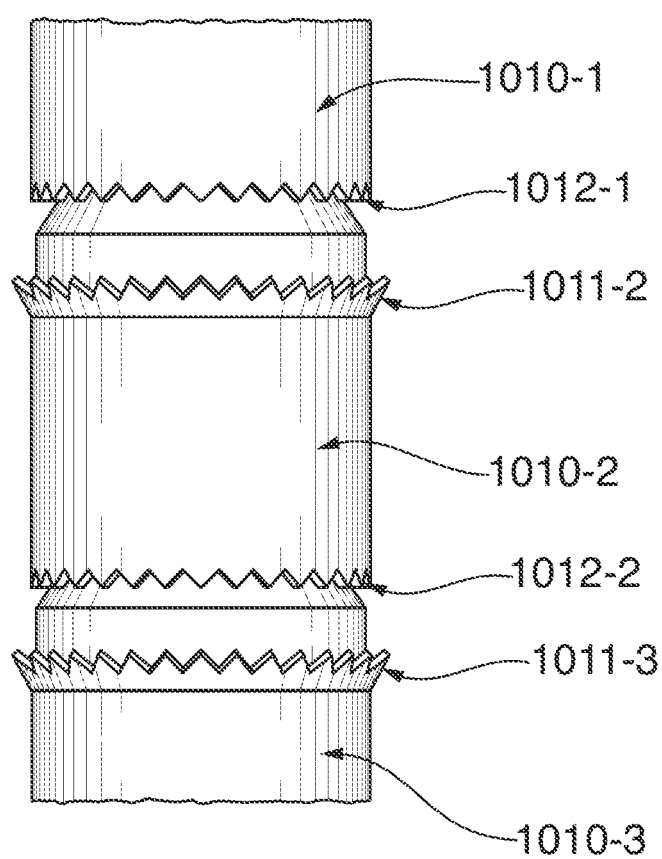

FIG. 10C depicts a detailed view of the cross section of an example embodiment of segments for use in an immobilization device with dentate peripheral projections. The segments 1010-1, 1010-2 and 1010-3 in FIG. 10C are similar to FIGS. 10A and 10B. However, segments 1010-1, 1010-2 and 1010-3 include a covering with dentate peripheral projections 1011-2, 1011-3, 1012-1 and 1012-2. Dentate peripheral projections 1011-2, 1011-3, 1012-1 and 1012-2 are an optional configuration of the segments 1010-1, 1010-2 and 1010-3 and limit rotation motions. The dentate peripheral projections 1011-2, 1011-3, 1012-1 and 1012-2 limit both bending and rotational forces, including those exceeding the friction force of segments when the system is activated. The dentate peripheral projections include teeth that interlock when the segments are compressed through activation, as described in FIGS. 1, 2, 5A, 5B and 11.

FIG. 11 depicts an example embodiment of an immobilization device 1100 with a vest 1140, a belt 1135 and caudal extension 1137, and showing pillars 1150-1, 1150-2, 1150-3 and 1150-4 with exposed segments. The immobilization device 1100 shares many components with the immobilization devices depicted in FIGS. 1 and 2. The immobilization device 1100 includes a helmet 1110, a vest 1140 and pillars 1150-1, 1150-2, 1150-3 and 1150-4. The helmet 1110 includes helmet attachment points 1112-1 and 1112-2. The vest 1140 includes a back vest portion 1145-1 and a front vest portion 1145-2, attachment points 1120-1 and 1120-2, chest straps 1141-1, 1141-2, 1141-3 and 1141-4. The helmet 1110 attaches to the vest 1140 with pillars 1150-1 and 1150-2. The vest 1140 attaches to the belt at belt attachment point 1132.

The immobilization device 1100 includes pillars 1150-1, 1150-2, 1150-3 and 1150-4 where the individual segments are visible in the pillars. However, in other embodiments the segments will be covered with a sheath or outer covering to avoid wear on the segments and to avoid blocking or hindering the operation of the segments, for example through clothing being caught in-between segments when the immobilization device is activated. The segments used in pillars 1150-1, 1150-2, 1150-3 and 1150-4 can be any of those described in reference to FIGS. 3A and 3B, 4, 5A, 5B, 10A, 10B and 10C. The segments in pillars 1150-1, 1150-2, 1150-3 and 1150-4 may be locked in place with a locking mechanism that can be in attachment point 1120-1, 1120-2 and/or belt attachment point 1132. The locking mechanism can be any of those described in reference to FIGS. 6, 7, 8A and 8B. Further detail on the caudal extension 1137 can be seen in reference to FIG. 9. The immobilization device 1100 can be activated as described in reference to FIGS. 1, 2, 5A and 5B.

The back vest portion 1145-1 and a front vest portion 1145-2 will typically be constructed of a durable and non-flexible material. For example, lightweight metals, composite materials, ceramics can be used depending on the application. In certain applications, the back vest portion 1145-1 and front vest portion 1145-2 will also serve as protections from ballistics, such as protection from bullets or protection from debris from a blast. The back vest portion 1145-1 and front vest portion 1145-2 may be contoured in some applications to fit more comfortably against the user. Furthermore, in some example applications, the back vest portion 1145-1 and front vest portion 1145-2 will be embedded within a flexible and comfortable material, such as cloth and worn as clothing.

In reading the above description, persons skilled in the art will realize that there are apparent variations that can be applied to the methods and systems described. In the foregoing specification, the invention has been described with reference to specific exemplary embodiments thereof. It will, however, be evident that various modifications and changes may be made to the specific exemplary embodiments without departing from the broader spirit and scope of the invention as set forth in the appended claims. Accordingly, the specification and drawings are to be regarded as illustrative rather than restrictive. Furthermore, a person of ordinary skill in the art would understand that aspects related to a specific embodiment can also be applied to other disclosed embodiments.

What is claimed is:

1. A rapid activation immobilization system, comprising:
    a helmet including a cranial attachment point;
    a harness including a thorax attachment point; and
    a pillar connected at a first end to the cranial attachment point of the helmet and at a second end to the thorax attachment point of the harness, the pillar including:
       a flexible sleeve,
       a plurality of segments each with a cylindrical shape and a circular cross section and each including hollow lumens centrally located on the cross section of the segments and running along a longitudinal axis of the segments, each segment having a first concave end and a second convex end, the circular cross section being uniform in diameter along at least a portion of a length of each segment between the first concave end and the second convex end,
       an inelastic wire extending through the hollow lumen of each of the plurality of segments; and
       a rapid locking mechanism connected to the inelastic wire;
    wherein the rapid locking mechanism operates to activate the rapid activation immobilization system by rapidly tightening the inelastic wire, thereby shortening the length of the inelastic wire and compressing the plurality of segments, causing the plurality of segments to interlock and form a rigid pillar of uniform circular cross section; and
    wherein, when the rapid activation immobilization is not activated, the rapid activation immobilization system is configured to accommodate a full range of motion of a user, such that the pillar remains flexible and configured to allow swiveling and rotating of a head of the user.

2. A rapid activation immobilization system as in claim 1, further comprising a second pillar.

3. A rapid activation immobilization system as in claim 1, wherein the locking mechanism is operable to use a piston and ratchet mechanism to tighten the wire.

4. A rapid activation immobilization system as in claim 1, further comprising an activation mechanism communicatively coupled to the locking mechanism, operable to activate the locking mechanism when the activation mechanism detects a rapid acceleration or a rapid deceleration.

5. A rapid activation immobilization system as in claim 4, wherein the activation mechanism includes a gyroscope for detecting the rapid acceleration or the rapid deceleration.

6. A rapid activation immobilization system as in claim 1, wherein the segments are each made of a single contiguous material.

7. A rapid activation immobilization system, comprising:
    a helmet including a cranial attachment point;
    a harness including a thorax attachment point; and
    a pillar connected at a first end to the cranial attachment point of the helmet and at a second end to the thorax attachment point of the harness, the pillar including:
       a plurality of segments each with a cylindrical shape and a circular cross section and each including hollow lumens centrally located on the cross section of the segments and running along a longitudinal axis of the segments, each segment having a first concave end and a second convex end, the circular cross section being uniform in diameter along at least a portion of a length of each segment between the first concave end and the second convex end;
       an inelastic wire threaded through the hollow lumen of each of the plurality of segments; and
       a rapid locking mechanism connected to the inelastic wire and including an electric motor and a gear connected to a coaxial gear;
    wherein the rapid locking mechanism operates to rapidly tighten the inelastic wire by winding the inelastic wire using an electric motor around the coaxial gear, thereby shortening the length of the inelastic wire and compressing the plurality of segments and causing the plurality of segments to interlock and form a rigid pillar of uniform circular cross section; and
    wherein, when the rapid activation immobilization is not activated, the rapid activation immobilization system is configured to accommodate a full range of motion of a user, such that the pillar remains flexible and configured to allow swiveling and rotating of a head of the user.

8. A rapid activation immobilization system as in claim 7, wherein the coaxial gear has a differential diameter.

9. A rapid activation immobilization system as in claim 7, wherein the diameter of the coaxial gear decreases as the inelastic wire is wound around the coaxial gear during operation to tighten the inelastic wire.

10. A rapid activation immobilization system as in claim 1, further comprising an activation mechanism including an accelerometer and a pressure sensor, the activation mechanism communicatively coupled to the locking mechanism, where the accelerometer and pressure sensor are configured to detect effects of an explosion and the activation mechanism is operable to activate the locking mechanism in a manner sufficiently rapid to counter act the effects of the explosion on the user of the activation immobilization system.

11. A rapid activation immobilization system as in claim 1, wherein the length of the plurality of segments is configured to according to the user.

12. A rapid activation immobilization system as in claim 1, wherein the harness includes a housing with the rapid locking mechanism and is configured to be located at a thoracic spine region of the user of the rapid activation immobilization system.

13. A rapid activation immobilization system as in claim 1, wherein the thorax attachment point is configured to be at a thoracic spine region of the user.

14. A rapid activation immobilization system as in claim 3, further comprising a chemical charge operable to push the piston through an explosion when the chemical charge is activated, and wherein the piston is connected to the inelastic wire, and is operable to rapidly tighten the wire as a result of the force resulting from the activation of the chemical charge moving the piston relative to the ratchet.

15. A rapid activation immobilization system as in claim 3, further comprising a compressed gas chamber in the harness, wherein the compressed gas chamber is operable to push the piston with a gas released into the compressed gas chamber, and wherein the piston is connected to the inelastic wire, and is operable to rapidly tighten the wire as a result of the force resulting from the gas causing a rapid moving the piston relative to the ratchet.

16. A rapid activation immobilization system as in claim 1, wherein the plurality of segments include an enamel on the surfaces of the first concave end and the second convex end, wherein the enamel increases the friction between the plurality of segments when the plurality of segments interlock.

* * * * *